(12) United States Patent
Beekman (10) Patent No.: US 12,082,960 B2
(45) Date of Patent: Sep. 10, 2024

(54) X-RAY IMAGING APPARATUS AND METHODS

(71) Applicant: MILABS B.V., Houten (NL)

(72) Inventor: Frederik Johannes Beekman, Utrecht (NL)

(73) Assignee: MILABS B.V., Houten (NL)

( * ) Notice: Subject to any disclaimer, the term of this patent is extended or adjusted under 35 U.S.C. 154(b) by 271 days.

(21) Appl. No.: 17/629,833

(22) PCT Filed: Aug. 10, 2020

(86) PCT No.: PCT/EP2020/072414
§ 371 (c)(1),
(2) Date: Jan. 25, 2022

(87) PCT Pub. No.: WO2021/037545
PCT Pub. Date: Mar. 4, 2021

(65) Prior Publication Data
US 2022/0257205 A1    Aug. 18, 2022

(30) Foreign Application Priority Data
Aug. 23, 2019 (NL) ...................... 2023695

(51) Int. Cl.
*A61B 6/00*         (2024.01)
*A61B 6/06*         (2006.01)
(Continued)

(52) U.S. Cl.
CPC ............. *A61B 6/4441* (2013.01); *A61B 6/06* (2013.01); *A61B 6/4411* (2013.01); *A61B 6/508* (2013.01); *A61B 6/5205* (2013.01); *G21K 1/025* (2013.01)

(58) Field of Classification Search
CPC ......... A61B 6/5205; A61B 6/06; A61B 6/508; A61B 6/4411; A61B 6/4441; A61B 6/032;
(Continued)

(56) References Cited

U.S. PATENT DOCUMENTS 5,966,424 A     10/1999  Liu
7,940,890 B1 *  5/2011   Linev ...................... A61B 6/502
                                                      378/146
(Continued)

OTHER PUBLICATIONS

Dutch Search Report, issued in Priority Application No. 2023695, dated May 27, 2020.
(Continued)

*Primary Examiner* — Irakli Kiknadze
(74) *Attorney, Agent, or Firm* — Birch, Stewart, Kolasch & Birch, LLP (57) ABSTRACT

An x-ray imaging apparatus for producing an x-ray image of an object, includes a support frame to which an x-ray source and an x-ray detector are connected. The x-ray source and the x-ray detector define between them an object space for the object to be examined. The x-ray source is configured to emit from a focal spot an x-ray beam with a main direction into the object space. The x-ray detector includes an array of pixels sensitive to the x-ray radiation. The x-ray imaging apparatus further includes a collimator arranged in proximity to the x-ray source and in the path of the x-ray beam between the x-ray source and the object to be examined. The collimator includes one or more collimator bodies defining a plurality of passages of the collimator, the passages having respective central directions defining a common focal point of the collimator on the side of the x-ray source, preferably a 2D array of passages seen in a plane perpendicular to the main direction of the x-ray beam.

15 Claims, 2 Drawing Sheets

(51) Int. Cl.
*A61B 6/50* (2024.01)
*G21K 1/02* (2006.01)

(58) Field of Classification Search
CPC ... A61B 6/4452; A61B 6/4291; A61B 6/4021; A61B 6/03; A61B 6/4233; A61B 6/469; A61B 6/5282; A61B 6/4007; A61B 6/482; A61B 6/405; A61B 6/502; A61B 6/4035; A61B 6/4266; A61B 6/00; A61B 6/025; A61B 6/4241; A61B 6/4429; A61B 6/5235; A61B 6/5241; A61B 6/54; G21K 1/025; G21K 1/043; G21K 1/04; G01T 1/2985; G01T 1/243; G01N 23/044; G01N 23/046; G06T 11/005; G06T 11/003; H05G 1/64
USPC .......................... 378/4, 11, 19, 62, 147–153
See application file for complete search history.

(56) References Cited

U.S. PATENT DOCUMENTS

| | | | | |
|---|---|---|---|---|
| 2002/0015474 | A1* | 2/2002 | Tybinkowski | G21K 1/025 378/147 |
| 2006/0008047 | A1* | 1/2006 | Zhou | G01N 23/046 378/10 |
| 2010/0202591 | A1 | 8/2010 | McKim et al. | |
| 2012/0087462 | A1* | 4/2012 | Ikhlef | G21K 1/025 378/4 |
| 2013/0114796 | A1* | 5/2013 | Funk | G21K 1/025 378/149 |
| 2014/0119508 | A1* | 5/2014 | Kang | G21K 1/04 378/150 |

OTHER PUBLICATIONS

International Search Report, issued in PCT/EP2020/072414, dated Nov. 6, 2020.
Written Opinion of the International Searching Authority, issued in PCT/EP2020/072414, dated Nov. 6, 2020.
Zhu et al., "An approach to increasing the resolution of industrial CT images based on an aperture collimator", Optics Express, Nov. 7, 2013, vol. 21, No. 23, total 18 pages.

* cited by examiner

X-RAY IMAGING APPARATUS AND METHODS

CROSS REFERENCE TO RELATED APPLICATIONS

This application is the National Phase of International Application No. PCT/EP2020/072414, filed on Aug. 10, 2020, which claims priority to application no. 2023695, filed in The Netherlands on Aug. 23, 2019.

FIELD OF THE INVENTION

The present invention relates to an x-ray imaging apparatus for producing an x-ray image of an object, comprising:
a support frame to which an x-ray source and an x-ray detector are connected,
wherein the x-ray source and the x-ray detector define between them an object space for the object to be examined, the x-ray source being configured to emit from a focal spot an x-ray beam with a main direction into the object space, the x-ray detector comprising an array of pixels sensitive to the x-ray radiation.

Such x-ray imaging apparatuses are generally known and are used for examining an object, e.g. a biological object, e.g. a small animal, or a sample, by means of sending a beam of x-ray radiation through the object, and detecting the radiation after being attenuated by the object.

BACKGROUND OF THE INVENTION

A problem of known x-ray imaging apparatuses is that they do not always provide detected images with a sufficiently high resolution, especially not if the dimensions of the objects to be examined varies relatively widely, and more in particular if they become relatively small with respect to the x-ray source. The latter is, for instance, of relevance in small animal imaging wherein internal organs or structures within the animal, e.g. mouse, may be very small. Some x-ray sources are known in which the focal spot, or area from which the photons are emitted, is itself small, or is switchable between a large and a small spot. These small focal spot x-ray sources may be impractical in that they are often rather bulky, e.g. because the 'electron accelerator' or voltage source then often is positioned directly behind the source's anode, which is undesirable, and they often have a relatively short useful life, due to much increased wear.

OBJECT OF THE INVENTION

It is therefore generally an object of the present invention to provide an x-ray imaging apparatus of the kind mentioned above, that is able to provide high resolution images even for small objects, e.g. in small animal imaging.

It is another object of the invention to enable the use of compact and/or long-life x-ray sources, that still have a high resolution.

SUMMARY OF THE INVENTION

The invention provides for an x-ray imaging apparatus for producing an x-ray image of an object, comprising:
a support frame to which an x-ray source and an x-ray detector are connected,
wherein the x-ray source and the x-ray detector define between them an object space for the object to be examined, the x-ray source being configured to emit from a focal spot an x-ray beam with a main direction into the object space, the x-ray detector comprising an array of pixels sensitive to the x-ray radiation,
the x-ray imaging apparatus further comprising a collimator arranged in proximity to the x-ray source and in the path of the x-ray beam between the x-ray source and the object to be examined, the collimator comprising one or more collimator bodies defining a plurality of passages of the collimator, the passages having respective central directions defining a common focal point of the collimator on the side of the x-ray source.

The x-ray imaging apparatus according to the invention may achieve one or more of the objectives because the collimator may serve as a means to select only a relatively small part of the x-ray source's focal spot. Ordinarily, such an x-ray source is an x-ray tube that has an emitting area with certain dimensions, the focal spot, that are not negligibly small with respect to the structures in the object to be examined, in particular the desired details thereof, and hence the resolution obtainable is often insufficient. By using the inventive collimator arrangement in proximity of the x-ray source, which arrangement has passages whose central directions originate from a focal point or rather a focal volume as will be explained herein, the apparent dimension(s) of the x-ray focal spot is (are) further reduced. In fact, the effective dimensions become close to the dimensions of the focal point or volume of the collimator. These dimensions, depending on the properties of the collimator, may in embodiments be limited to a small number of μm's for imaging of small animals, or a fraction of an mm for a clinical X-ray system or CT scanner.

In theory, it is possible to have all central directions of the passages of the collimator originate exactly from one point, the focal point. However, in practice the x-rays emerging from a passage will still be distributed over a band of directions around the central direction of that passage. This means that the apparent origin of the x-rays emerging from a single passage is also a "smeared out" focal point, i.e. a focal volume. Yet, because each passage will have a non-negligible length, this distribution, i.e. the size of the focal volume, may be substantially smaller than the original focal spot area of the x-ray source.

According to the invention, the collimator is positioned in proximity of the x-ray source and in between the x-ray source and the object to be imaged. In practice, the collimator will be positioned very close to the x-ray source, in particular as close to the x-ray source as possible. In practical embodiments, the x-ray source is an x-ray tube that has a housing including an x-ray window from which the x-ray beam leaves the x-ray source, wherein the collimator is arranged outside of the window, in proximity to the window, e.g. a beryllium window.

As preferred, the collimator, and any collimator mover when present, is mounted to the support frame, e.g. on the x-ray source and/or in vicinity of the x-ray source. For example, in embodiments wherein the support frame is movable by a support frame drive to bring the x-ray source in various spatial positions relative to the object space, the collimator then follows motion of the support frame and remains in proximity to the x-ray source and in the path of the x-ray beam between the x-ray source and the object to be examined.

The distance of the collimator to the x-ray source is, preferably, a fixed distance, e.g. in view of positioning the focal point of the passage of the collimator in the actual focal spot of the x-ray source. For example, the collimator is movable by an associated mover in a direction or plane that extends perpendicular to the x-ray beam, yet is not movable towards and away from the x-ray source along the direction of the x-ray beam.

It is preferred for the common focal point of the plurality of passages of the collimator to be located on the focal spot of the X-ray source.

It is preferred for the common focal point of the plurality of passages of the collimator to have an effective size that is smaller than the focal spot of the X-ray source, e.g. an effective size with a diameter between 10 µm and 50 µm, e.g. for small animal imaging.

In an embodiment, the passages of the collimator each have a diameter or largest cross-sectional dimension of between 1 µm and 10 µm, e.g. between 1 µm and 5 µm, e.g. for small animal imaging.

A collimator in an x-ray imaging apparatus according to the invention comprises a collimator body, or sometimes a number of collimator bodies, that either by themselves or in combination define(s) passages or through going holes for the x-ray. In between the passages is x-ray blocking material of the collimator, such that there are some directions, corresponding to the blocking material, in which no radiation is effectively emitted from the x-ray source when the collimator is in its operative position. To compensate for this effect, and in order to obtain information from those directions as well, it is highly preferred for the collimator to be movable by means of an associated collimator mover, that is configured to move the collimator. For example, the mover is embodied to move the collimator in two directions perpendicular to the x-ray beam direction. In practical embodiments, the displacement of the collimator need not be (much) more than the centre-to-centre distance of the passages and can even be the same or even less than said distance in embodiments, e.g. half said distance or about said distance.

Of course, positioning such a collimator in the x-ray beam path reduces the intensity of the x-rays, and this can be compensated by a prolonged exposure time. It may be necessary to ensure that the object does not move during the prolonged exposure. But note that it is often tissue parts of an object that needs to be examined or an anesthetized object, in which case there is no motion blur during prolonged exposure. This likewise indicates that the absolute dimensions of the actual object (e.g. an organ or a limb of an animal) often much smaller than an ordinary object, i.e. the full animal.

In an embodiment, the x-ray imaging apparatus further comprises a collimator mover configured to move the collimator with respect to the x-ray source in at least two directions, e.g. orthogonal directions, in a plane perpendicular to the main direction of the x-ray beam.

For example, the collimator mover is configured to provide solely for a planar motion of the collimator with respect to the x-ray source in at least two directions, e.g. orthogonal directions, in a plane perpendicular to the main direction of the x-ray beam. This solution has a low complexity.

It is envisaged that the collimator mover is configured and operated to move the collimator during producing of one x-ray image into multiple distinct positions in the course of acquisition of data related to said one image. For example, the collimator has in one direction perpendicular to the x-ray beam an array of multiple passages at a centre-to-centre spacing at the incident side of the collimator, wherein the collimator mover is configured and operated to move the collimator in said one direction between two acquisition positions over a distance that is related to said centre-to-centre distance, e.g. over a distance of between 0.5 and 2 times said centre-to-centre distance, e.g. 1 times said centre-to-centre distance, e.g. in the course of acquisition of data related to one image, e.g. from one spatial location of the x-ray source relative to the object to be examined.

In an embodiment, the collimator mover is configured to move and is operated to move the collimator over an area of an imaginary sphere relative to the common focal point.

In an embodiment, the collimator mover comprises one or more piezo-actuators to provide for motion of the collimator, e.g. configured and operated to move the collimator during producing of one x-ray image into multiple distinct positions in the course of acquisition of data related to said one image.

In an embodiment, the collimator has in one direction perpendicular to the x-ray beam an array of multiple passages at a centre-to-centre spacing at the incident side of the collimator, wherein the collimator mover is configured to move and is operated to move the collimator in said one direction over a distance related to said centre-to-centre distance, e.g. over a distance of between 0.5 and 2 times said centre-to-centre distance, e.g. 1 times said centre-to-centre distance.

Particular embodiments are described in the dependent claims, as well as in the now following part of the description.

In embodiments, the support frame is movable relative to a stationary main frame by a support frame drive.

In embodiments, the object carrier is movable relative to a stationary main frame by an object carrier drive, preferably independently controllable from motion of the support frame effected by a support frame drive.

In embodiments, the support frame is rotatable, by an associated drive, about an axis extending through the object space, e.g. a horizontal axis. This, for example, may allow for creating 3D imaging capability.

In embodiments, the x-ray imaging apparatus further comprises a main frame, e.g. a stationary main frame, to which the support frame is mounted, as well as an object carrier for carrying the object in the object space. In embodiments, the support frame and the object carrier are rotatable with respect to each other.

The object may be positioned on an object carrier such as an, optionally movable, object table or other carrier, or may be held by one or more wires or the like.

The object carrier may be part of the x-ray imaging apparatus, or may be a distinct device that is removable and insertable from and into the object space.

The support frame may be rotatable with respect to a stationary main frame and/or the object carrier may be rotatable with respect to the support frame, e.g. in order to obtain 3D capabilities for the imaging. However, it is also useful to have only one imaging direction, i.e. 2D imaging only.

In some embodiments, the collimator is removably positionable in an operative position. Providing a removable collimator, that is actually removable out of the way of the x-ray beam all together, makes it possible to use the "normal" x-ray source for relatively large objects or parts thereof, while—if a higher resolution is needed, such as in particular for smaller details or objects,—the collimator is put into its operative position. In the operative position, in embodiments, the collimator mover may be present to perform collimator motion as described herein for acquisition of data related to establishing an x-ray image.

In embodiments, the x-ray imaging apparatus further comprises a collimator remover device for automated motion of the collimator between an operative position and an inactive position where the collimator is out of the beam of x-rays. By automatizing this motion for removal of the collimator, and of course conversely the moving into operative position, of the collimator, it becomes possible to switch to a different resolution during examining one and the same object.

In embodiments, the collimator comprises a cone beam collimator with a plate body having a 2D array of holes therein, wherein all holes are directed towards the common focal point and form said plurality of passages of the collimator. This type of collimator is per se well-known, and is now used close to the x-ray source in order to select a small part of the focal spot to emit the effective x-ray beam. Such a cone beam collimator may be made by making passages in a plate of material of about 0.5 mm to a few mm thickness, such as by laser drilling or Electric Discharge Machining. It is also possible to punch or otherwise provide holes in a plurality of thin plates, of say 0.1 mm thickness, which holes, when the thin plates are stacked, together form the passages of the collimator.

In an embodiment, the collimator comprises a cone beam collimator having a collimator plate body with a 2D array of holes through collimator plate body, wherein said holes are all directed towards the common focal point and form said plurality of passages of the collimator. In an embodiment, the holes each have a diameter between 1 µm and 10 µm, e.g. between 1 µm and 5 µm.

In alternative or supplementary embodiments, the collimator comprises a set composed of a first collimator body and a second collimator body that is arranged in series with the first collimator body, wherein the first collimator body comprises multiple first apertures therein, wherein the second collimator body comprises multiple second apertures therein, and wherein said first and second apertures together form said plurality of passages of the collimator.

In an embodiment, the collimator comprises a set of a first collimator body and a second collimator body arranged in series with the first collimator body, wherein the first collimator body comprises a first stack of spaced apart first plates with respective first slits spaces there between, said first slit spaces being directed towards a common first imaginary line, wherein the second collimator body comprises a second stack of spaced apart second plates with respective second slit spaces there between, wherein said second slit spaces are directed towards a common second imaginary line, the first and second common imaginary lines crossing one another in the common focal point, so that the first and second slit spaces together form said plurality of passages of the collimator. This structure resembles somewhat a slit-slat collimator and has the advantage of being easy to produce. The structure has substantially square or rectangular passages, which may produce partial images that fit better onto a detector. For example, each collimator body of is made by stacking a plurality, e.g. at least three, plates of a material that is opaque for x-rays, such as gold or some other metal, with interposition of plates of an x-ray transparent material, such as many plastics, e.g. polystyrene. Another option would be to take a block of x-ray transparent material and create slits in the material, such as by milling or lasering, after which these slits are filled with an x-ray opaque material. Other production methods are not excluded, e.g. 3D printing.

The way in which the collimator moves the collimator or one or more collimator bodies thereof relative to the x-ray source is not particularly limited. In practice one would like to provide a motion that ensures that x-ray radiation from a sufficient amount of angles is imaged through the object.

Preferably, the collimator mover is arranged to move the collimator during imaging in two different directions, preferably consecutively, which directions are substantially perpendicular to the main direction of the x-ray beam, e.g. orthogonal to one another. Each said motion may be over a distance that relates to a centre-to-centre distance between two passages that are neighboring in said direction, e.g. half said distance, or about or exactly said distance, or a few times said distance.

In practice it is desired to move the collimator such that all of the radiation coming from the focal point/volume, not from the larger focal spot of the x-ray source, can pass at least one passage of the collimator.

It may be possible to use a respective distance that is equal to the centre-to-centre distance minus the width of the passage, in each case at the side of the x-ray source.

It is remarked that in a particular embodiment the moving by the collimator mover of the collimator or each of the one or more collimator body/bodies is performed over an imaginary spherical surface that extends around the focal point, so having the focal point as centre of the radius. This is done, for example, in view of the spherical symmetry of the x-ray beam. With strictly planar displacements of the collimator, the focal point would then move across the focal spot of the x-ray source, which may lower the resolution. The collimator and associated mover are, in embodiments, configured for performing such a spherical movement (e.g. over a grid of geodesics across the spherical surface). This may be brought about by means of a mechanical coupling between movements, which are then effectively in three dimensions, or by means of electronically controlling separate movements in all directions.

The movement of the one or more collimator bodies relative to the x-ray source may be performed in steps, such as in a 'grid', in which firstly a number of images are taken at a starting position in the first direction, and with a step of displacing the collimator over a part of the desired total displacement in the second direction. Thereafter, a step is taken in the first direction, and again a number of images are taken by stepwise displacement in the second direction, and so on until also all desired steps in the first direction have been covered. For example, a grid of 4×4 steps will provide good results efficiently, although any other plurality of steps may also perform satisfactorily. It is also possible to perform a sweep in the second direction, i.e. imaging continuously while moving the collimator in the second direction, and after finishing the sweep to take a step in the first direction, repeating the sweep, and so on.

In an embodiment, the first collimator body and a second collimator body of the collimator are mobile relative to one another and/or relative to the x-ray source, e.g. in multiple positions relative to the x-ray beam in the course of acquisition of imaging data used to establish a single x-ray image.

In an embodiment, the first collimator body and a second collimator body are mounted to one another as an integrated collimator body, wherein said integrated collimator body is mobile relative to the x-ray source as described herein by a collimator mover.

In an embodiment, the first collimator body and a second collimator body are mobile relative to one another and relative to the x-ray source, wherein a first collimator body mover is connected to the first collimator body, and wherein a second collimator body mover is connected to the second collimator body, the first and second collimator body movers each being configured to move the respective collimator body. For example, one or both of the first and second collimator body movers are embodied as described herein.

In an embodiment, the collimator comprises a set of a first collimator body and a second collimator body that is arranged in series with the first collimator body, wherein the first collimator body comprises a first stack of spaced apart first plates with respective first slits spaces there between, said first slit spaces being directed towards a common first imaginary line, and wherein the second collimator body comprises a second stack of spaced apart second plates with respective second slit spaces there between, wherein said second slit spaces are directed towards a common second imaginary line, the first and second common imaginary lines crossing one another in the common focal point, so that the first and second slit spaces together form said plurality of passages of the collimator, and wherein the first collimator body and a second collimator body are mobile relative to one another and relative to the x-ray source, wherein a first collimator body mover is connected to the first collimator body and wherein a second collimator body mover is connected to the second collimator body, the first and second collimator body movers being configured to move the respective collimator body in a direction substantially perpendicular to the slits thereof. For example, one or both of the first and second collimator body movers are embodied as described herein.

It is possible, in embodiments, for the collimator movers to move one of the first or second body one step at a time, in a corresponding direction, and then between two subsequent steps move the other collimator body in another, e.g. perpendicular direction, by means of the other mover, all the while an x-ray image is being made.

The present invention also relates to the combination an x-ray source configured for use in x-ray imaging apparatus for producing an x-ray image of an object, the x-ray source being configured to emit from a focal spot an x-ray beam with a main direction into an object space of the x-ray imaging apparatus, and a collimator arranged in proximity to the x-ray source and in the path of the x-ray beam from the x-ray source to the object to be examined, the collimator comprising one or more collimator bodies defining a plurality of passages of the collimator, the passages having respective central directions defining a common focal point of the collimator on the side of the x-ray source, preferably a 2D array of passages seen in a plane perpendicular to the main direction of the x-ray beam. It will be appreciated that the combination may further be provided with one or more additional features as discussed herein.

The present invention also relates to a method for imaging an object by means of an x-ray imaging apparatus as described herein.

The present invention also relates to a method for retrofitting an x-ray imaging apparatus for producing an x-ray image of an object, which x-ray imaging apparatus comprises:
 a support frame to which an x-ray source and an x-ray detector are connected,
wherein the x-ray source and the x-ray detector define between them an object space for the object to be examined, the x-ray source being configured to emit from a focal spot an x-ray beam with a main direction into the object space, the x-ray detector comprising an array of pixels sensitive to the x-ray radiation,
wherein the method comprises the step of arranging a collimator in proximity to the x-ray source and in a path of the x-ray beam between the x-ray source and the object to be examined, the collimator comprising one or more collimator bodies defining a plurality of passages of the collimator, the passages having respective central directions defining a common focal point of the collimator on the side of the x-ray source, preferably a 2D array of passages seen in a plane perpendicular to the main direction of the x-ray beam, said collimator creating an effective focal spot that is smaller than the focal spot of the x-ray source.

The present invention also relates to a method to reduce the effective focal spot of an x-ray source in an x-ray imaging apparatus, wherein the method comprises the step of arranging a collimator in proximity to the x-ray source and in a path of the x-ray beam between the x-ray source and the object to be examined, the collimator comprising one or more collimator bodies defining a plurality of passages of the collimator, the passages having respective central directions defining a common focal point of the collimator on the side of the x-ray source, preferably a 2D array of passages seen in a plane perpendicular to the main direction of the x-ray beam, said collimator creating an effective focal spot that is smaller than the focal spot of the x-ray source.

The invention will now be explained with reference to a number of non-limiting, exemplary embodiments, and to the drawings.

DETAILED DESCRIPTION OF EMBODIMENTS

Figure 1:
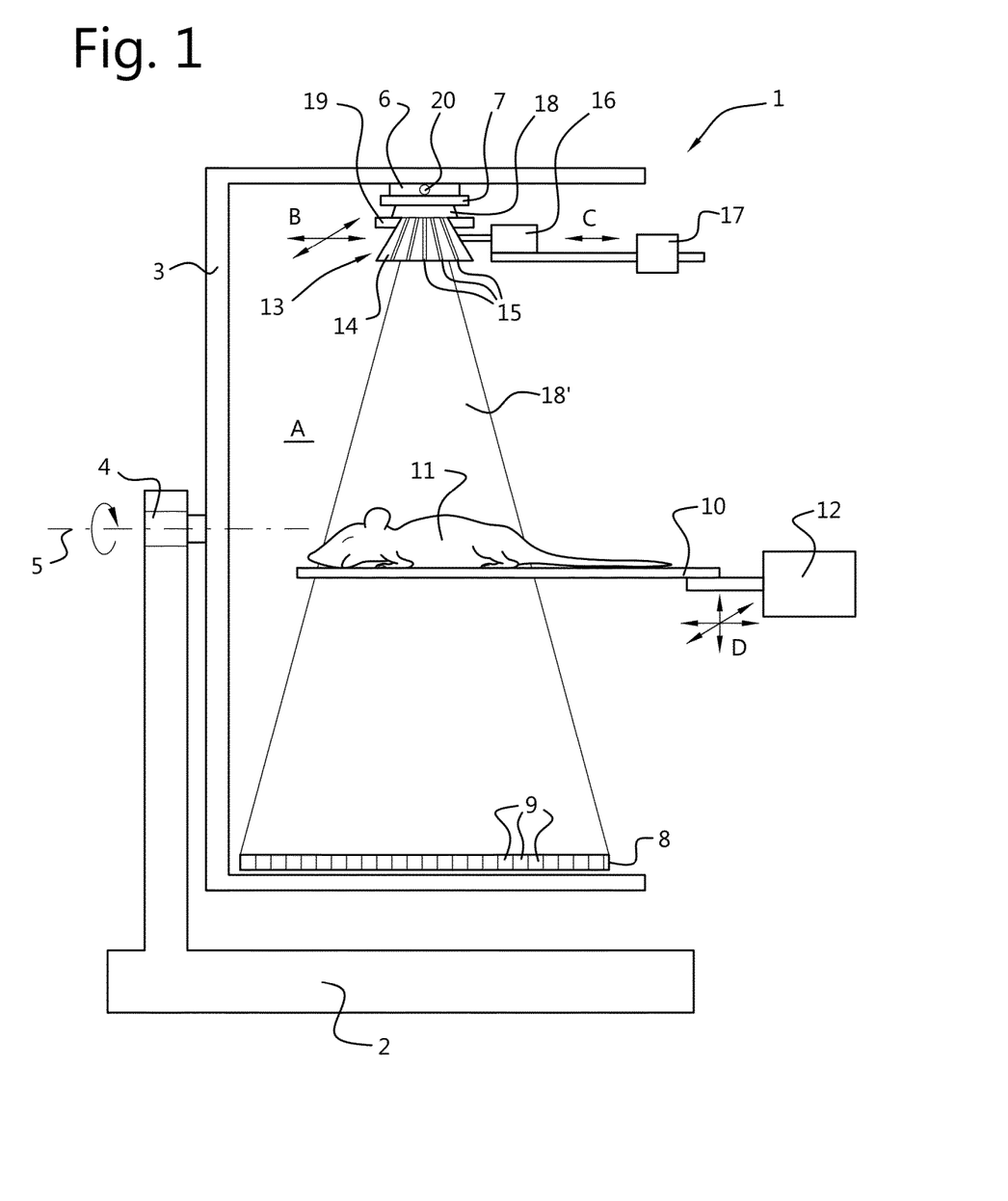
FIG. 1 shows very diagrammatically a first embodiment of an x-ray imaging apparatus according to the invention, in a side elevational view.

FIG. 1 shows very diagrammatically a first embodiment of an x-ray imaging apparatus 1 according to the invention, in a side elevational view.

The x-ray imaging apparatus 1 comprises a stationary main frame 2, to which is mounted a mobile, preferably rotatable support frame 3, e.g. embodied as a C-arm as shown here schematically, or embodied as a rotating gantry.

The support frame 3 is rotatable, preferably at least in a stepwise mode, by means of support frame rotator 4 around an axis 5, e.g. about a single axis, e.g. as in a gantry imaging system. In practical embodiments, the axis 5 is a horizontal axis.

An x-ray tube is indicated by reference numeral 6. Generally the x-ray tube 6 comprises an anode, an emitter arrangement comprising a cathode for emitting an electron beam towards the anode onto a focal spot on the anode, e.g. including electron optics for focusing the electron beam at the focal spot on the anode.

The x-ray tube 6 is provided with an X-ray window, e.g. a beryllium window 7.

An object carrier 10 is configured to carry an object 11 to be examined, e.g. a small animal, here a mouse.

An x-ray detector 8 is arranged for detecting at least part of the X-ray beam that has passed through the object 11.

Reference A indicates the object space between the x-ray tube 6 and the x-ray detector 8, wherein generally the object 11 to be examined is placed.

The x-ray detector 8 comprises an array, e.g. a 2D array, of pixels 9 sensitive to the x-ray radiation.

For example, the object carrier 10 comprises a horizontal table on which an object 11 to be examined is placed.

Preferably, the object carrier 10 is movable by means of an associated object carrier mover 12, here a table mover 12, between a retracted position outside the object space A and an imaging position within the object space A.

Preferably, the object carrier 10 is movable by means of an associated object carrier mover 12, here a table mover 12, in one or more directions whilst the carrier 10 supports the object in the object space, e.g. in multiple orthogonal directions, e.g. in x, y, z directions, e.g. as indicated by arrows D. These one or more direction motions can be performed before, during and/or after scanning the object with the apparatus.

A computerized reconstructor reconstructs the imaging data and may, in embodiments, be configured to generate three dimensional (3D) volumetric image data indicative of an examination region and an object therein. The resulting volumetric image data can be processed by an image processor or the like to generate one or more images.

A general purpose computing system may be provided to serve as an operator console, and includes an output device such as a display and an input device such as a keyboard, mouse, and/or the like. Software resident on the console may allow the operator to control the operation of the imaging device, for example, allowing the operator to initiate scanning, etc.

In front of the window 7 there is provided a collimator 13, that has a collimator body 14 with through going passages 15, and which is movable in the direction of arrows B by collimator mover 16.

A collimator remover 17 may remove the collimator 13 from the emitted x-rays 18 in the direction of arrows C.

A beam shaping and blocking device is designated '19'.

A narrowed and more focused beam is indicated 18', while a focal point of the beam 18' is designated '20'.

In use, an object 11, such as a mouse or the like, is provided on the object carrier or table 10, and moved into the object space "A" by means of the table mover 12. By moving the table 10 in any one or more of the directions indicated by the arrows D, the object 11 may be positioned as desired with respect to the x-ray source 6 and the detector 8, i.e. with respect to the beam 18.

The x-rays 18 are generated by an x-ray source 6, in this case e.g. an x-ray tube, and emitted in a relatively coarse beam 18, for example with a size of its focal spot between about 0.1 and 1.2 mm diameter, depending on the properties of the source 6.

Using the inventive collimator, the coarse x-ray beam 18 emitted by the source 6 is trimmed down and shaped to a beam 18' that seems to originate from a much smaller effective focal spot defined by focal point or focal volume 20. This effective focal spot or volume could, for example, have a size of 20-25 µm diameter. Thereto, the coarse radiation 18 is sent through the collimator 13, with the collimator body 14 that has through going holes or passages 15.

In the example shown, the collimator is a cone beam collimator, in which there is one collimator body 14, and all holes or passages point to the same focal point on the focal spot 20.

Optionally, there is provided an additional beam shaping and blocking device 19, which is in principle not much more than a rim around the collimator body 14, that blocks any superficial radiation. The presence of such a simple rim, which may be as thick as the rest of the collimator body 14, ensures that there will be no x-rays apart from the ones in the beam 18', without having to provide too many holes 15 in the rim of the collimator body 14.

In use of the x-ray imaging apparatus 1, the collimator 13 may be moved with respect to the source 6 by means of the collimator mover 16, e.g. in the direction of the arrows B. Note that the collimator 13 need not be moved more than the centre-to-centre distance between the passages 15 in order to provide a full image.

To increase precision, it is preferred for the collimator 13 to be moved on an imaginary sphere around the focal point 20, such that the effective position of that focal point 20 remains the same during imaging. The collimator mover and control thereof should then of course be laid out correspondingly. This may be achieved by mechanical means or by adding movability in the third dimension and having the collimator mover 16 perform the desired combined spherical movement of the collimator 13, in casu of the collimator body 14.

The collimator mover 16 may comprise one or more piezo-actuators to provide for the movability. Such actuators can provide small required displacements with high precision, reliability and repetition frequency. Yet, other actuators are not excluded, such as stepper motors.

The collimator remover 17 is shown as being provided to remove the collimator 13 from the x-ray beam 18/18'. In that case, the shaped beam 18' is then replaced again by the "coarse" x-rays 18, for example to image and examine much bigger objects 11, or with much higher intensity and correspondingly shorter exposure times. The collimator remover may comprise a coarser actuator than for the collimator mover 16, but it is also possible to combine the collimator mover and the collimator remover into one, such as with a device combining a piezo-actuator and a hinge or a linear actuator with a much larger stroke.

It is important to note that the drawing is not to scale. In particular, the dimensions of the object space A, that is, the distance between the x-ray tube 6 and the detector 8 are often between about 200 and 600 mm. Contrarily, the thickness of the collimator body 14 may in practice be about 1-2 mm. A larger thickness might not improve the qualities any further, but would make it more difficult to make the holes or passages 15.

Also the number of passages 15 in the collimator body 14 will be (much) higher than the five shown here. The diameter of each of the passages 15 in reality will be a few µm, such as between 1 and 10 µm. Together, they ensure that the focal spot 20 of the x-ray tube 6 will effectively be reduced to a focal volume pf a few dozen µm, such as e.g. 25 µm across. Similarly, the pixels 9 of the x-ray detector 8 are often somewhat less than 0.1×0.1 mm, such as 75 µm×75 µm, their number correspondingly higher than shown in the drawing. In all cases, the numbers are exemplary, only giving an impression of realistic values.

Furthermore, while a whole mouse 11, or at least a large part of it, may be examined in the present situation, it is possible to bring the object 11 much closer to the x-ray source 6, the collimator 13 still being between the source 6 and the object 11. It will be so that often a correspondingly smaller object or part thereof may be examined. Because of the much larger magnification (ratio between "distance from source 6 to object 11" to "distance from source 6 to detector 8"), it becomes more important to have a high resolution in the image. This is possible with the present invention due to the provision of the collimator 13 between the source 6 and the object 11, which reduces the effective size (focal spot) of the x-ray source from, say, 0.1 to 2 mm to, say, 25 µm. Note that, when bringing the object 11 closer to the source 6, it may be necessary to adapt the way in which the frame 3 with source 6 and detector 8 is rotated around an axis through the object 11, in order to obtain sufficient angular information. This adaptation may comprise sliding the support frame 3 in a direction perpendicular to the direction of the axis 5, such that the x-ray source 6 comes much closer to the axis 5 than the detector 8. Any other measure that achieves the same effect is also possible here.

The support frame 3 is here shown to be rotatable with respect to the main frame 2, e.g. about a horizontal rotation axis. However, it is also possible to have a fixed frame 3 without the rotatability, and have the object carrier 10 rotate with respect to the frame 3, or even have no rotation at all and have only 2D imaging properties.

Figure 2:
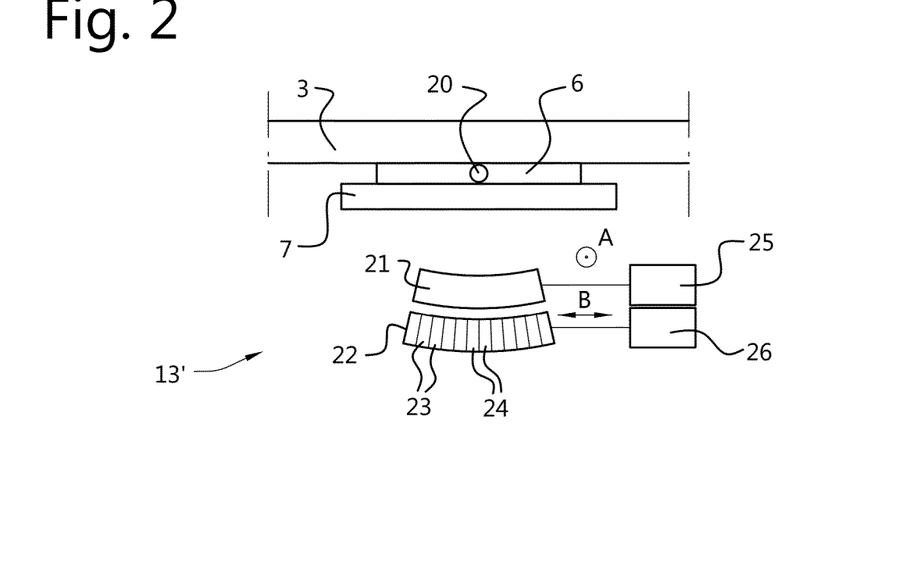
FIG. 2 shows a very diagrammatical detail of a different embodiment of the x-ray imaging apparatus according to the invention.

FIG. 2 shows a very diagrammatical detail of a different embodiment of the x-ray imaging apparatus according to the invention, in particular the part with the x-ray source and the collimator. Herein, as in all of the drawing, similar parts are denoted by the same reference numerals.

The detail shows a small part of the frame 3 with an x-ray source 6, a protective but x-ray transparent window 7, and a different collimator 13' having focal point 20 on the focal spot of the x-ray source 6.

The collimator 13' comprises a set of a first collimator body 21 and a second collimator body 22 that is arranged in series with the first collimator body 21. The first collimator body 21 comprises a first stack of spaced apart first plates 26 with respective first slit spaces 28 between adjacent plates. These first slit spaces 28 are all directed towards a common first imaginary line F1. The second collimator body 22 comprises a second stack of spaced apart second plates 23 with respective second slit spaces 24 there between. These second slit spaces 24 are all directed towards a common second imaginary line F2. The plates of the bodies are non-parallel from the one body to the other body, so that the first and second common imaginary lines cross one another in the common focal point 20. As a result the first and second slit spaces 28, 24 together form the plurality of passages of the collimator 13' focused on the common focal point 20, e.g. of very small size, e.g. much smaller than the focal spot of the x-ray source in absence of the collimator 13'.

The bodies 21, 22 may be moved by a corresponding mover 25, 26 about the respective focal line.

The bodies 21, 22 may interface with curved or even spherical adjoining sides as schematically illustrated, e.g. allowing for motion of each body about the respective focal line, e.g. by a corresponding mover 25, 26.

Figure 3:
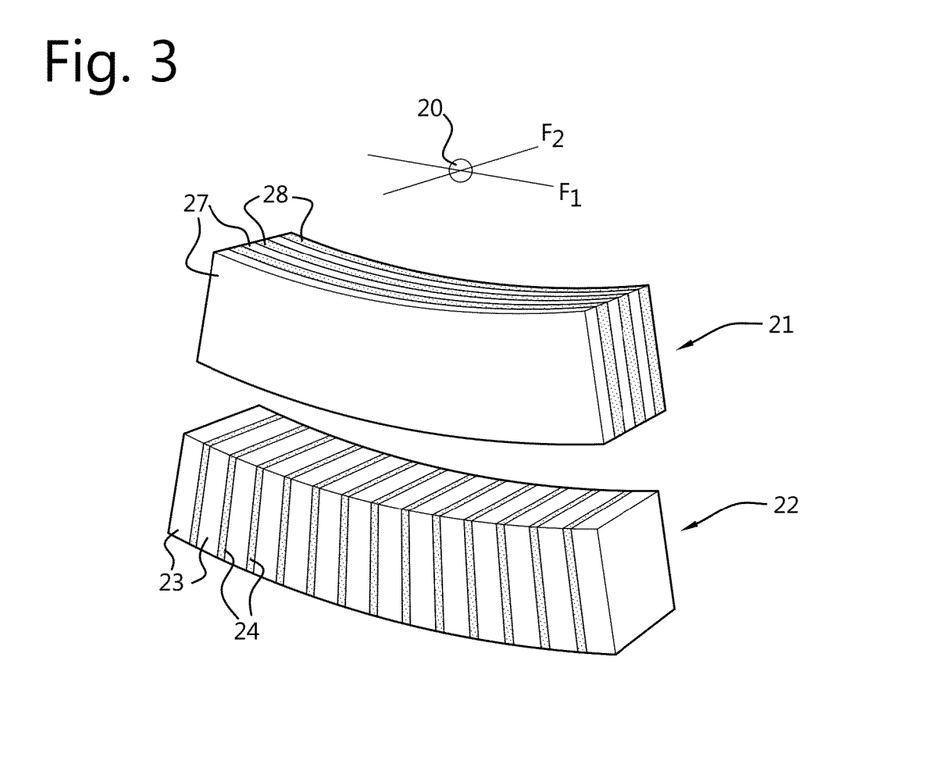
FIG. 3 shows the collimator of FIG. 2 in some more detail, in a diagrammatic perspective view.

FIG. 3 shows the collimator 13' in some more detail, in a diagrammatic perspective view.

When the beam of x-rays from the x-ray source 6 of FIG. 2 shines through this collimator 13', the resulting source as "seen" by an object is again an apparent focal spot 20, where the focal lines F1 and F2 cross.

The numbers of plates shown here by way of example is arbitrary, and these numbers, as well as the thickness of the plates 27, 23 and the width of the slits 28, 24 may be selected as desired.

The first collimator body mover 25 is arranged to move the first body 21, e.g. in a direction substantially perpendicular to the main direction of the corresponding slits 28, albeit in particular as preferred on a sphere around the focal point 20 or about line F1, i.e. the direction indicated by "A" in FIG. 2, which is into/out of the paper. Similarly, the second collimator body mover 26 may be arranged to move the second body 22 in the perpendicular direction of arrow B.

The movements of the two bodies 21, 22 may be coordinated, such as moving the first body 21 over a first step, and then performing a sweeping or further step like motion for the second body 22, or vice versa. Faster vibrating movements of both bodies 21, 22 during imaging are also possible, as long as all desired or possible beam directions originating from the focal point are imaged sufficiently. Note that the first and second collimator body movers may again comprise a piezo-actuator or the like, and may together be complemented by a collimator remover (not shown) for removing the collimator 13', likewise as for the collimator remover 17 as per FIG. 1.

The embodiments and figures are only given as an exemplifying explanation of the invention, without limiting the scope of the appended claims.

The invention claimed is:

1. An x-ray imaging apparatus for producing an x-ray image of an object, comprising:
   a support frame to which an x-ray source and an x-ray detector are connected,
   wherein the x-ray source and the x-ray detector define between them an object space for the object to be examined,
   the x-ray source being configured to emit from a focal spot an x-ray beam with a main direction into the object space,
   the x-ray detector comprising an array of pixels sensitive to the x-ray radiation,
   the x-ray imaging apparatus further comprising a collimator arranged in proximity to the x-ray source and in the path of the x-ray beam between the x-ray source and the object to be examined, the collimator comprising one or more collimator bodies defining a plurality of passages of the collimator, the passages having respective central directions defining a common focal point of the collimator on the side of the x-ray source, wherein the collimator comprises a set of a first collimator body and a second collimator body arranged in series with the first collimator body, wherein the first collimator body comprises a first stack of spaced apart first plates with respective first slit spaces there between, said first slit spaces being directed towards a common first imaginary line, and wherein the second collimator body comprises a second stack of spaced apart second plates with respective second slit spaces there between, wherein said second slit spaces are directed towards a common second imaginary line, the first and second common imaginary lines crossing one another in the common focal point, so that the first and second slit spaces together form said plurality of passages of the collimator.

2. The x-ray imaging apparatus according to claim 1, wherein the common focal point of the plurality of passages of the collimator is on the focal spot of the X-ray source.

3. The x-ray imaging apparatus according to claim 1, wherein the common focal point of the plurality of passages of the collimator has an effective size that is smaller than the focal spot of the X-ray source.

4. The x-ray imaging apparatus according to claim 1, wherein the common focal point of the plurality of passages of the collimator has an effective size with a diameter between 10 µm and 50 µm.

5. The x-ray imaging apparatus according to claim 1, wherein the x-ray source has a housing including an x-ray window from which the x-ray beam leaves the x-ray source, wherein the collimator is arranged outside of the window, in proximity to the window.

6. The x-ray imaging apparatus according to claim 1, wherein the x-ray imaging apparatus further comprises a collimator mover configured to move the collimator with respect to the x-ray source in at least two directions in a plane perpendicular to the main direction of the x-ray beam.

7. The x-ray imaging apparatus according to claim 6, wherein the collimator mover is configured to move the collimator over an area of an imaginary sphere relative to the common focal point.

8. The x-ray imaging apparatus according to claim 6, wherein the collimator mover comprises one or more piezo-actuators to provide for motion of the collimator.

9. The x-ray imaging apparatus according to claim 1, further comprising a main frame to which the support frame supporting the x-ray source and the x-ray detector is mounted, the support frame being rotatable about a rotation axis relative to the main frame.

10. The x-ray imaging apparatus according to claim 1, further comprising an object carrier configured for carrying an object in the object space.

11. The x-ray imaging apparatus according to claim 1, wherein the collimator is removably positionable in said position in proximity of the x-ray source, wherein the imaging apparatus comprises a collimator remover device configured for automated removing the collimator from said position to an inoperative position out of the x-ray beam.

12. The x-ray imaging apparatus according to claim 1, wherein the first collimator body and a second collimator body are mobile relative to one another.

13. The x-ray imaging apparatus according to claim 1, wherein the first collimator body and a second collimator body are mounted to one another as an integrated collimator body, and wherein the x-ray imaging apparatus further comprises a collimator mover configured to move said integrated collimator body relative to the x-ray source in at least two directions in a plane perpendicular to the main direction of the x-ray beam.

14. The x-ray imaging apparatus according to claim 1, wherein the first collimator body and a second collimator body are mobile relative to one another and relative to the x-ray source, wherein a first collimator body mover is connected to the first collimator body and wherein a second collimator body mover is connected to the second collimator body, the first and second collimator body movers being configured to move the respective collimator body.

15. The x-ray imaging apparatus according to claim 1, wherein the first collimator body and a second collimator body are mobile relative to one another and relative to the x-ray source, wherein a first collimator body mover is connected to the first collimator body and wherein a second collimator body mover is connected to the second collimator body, the first and second collimator body movers being configured to move the respective collimator body in a direction substantially perpendicular to the slits thereof.

* * * * *